United States Patent
Sinn et al.

(10) Patent No.: US 9,952,150 B2
(45) Date of Patent: Apr. 24, 2018

(54) DEVICE FOR MEASURING THE SCATTERING OF A SAMPLE

(71) Applicant: L.U.M. GmbH, Berlin (DE)

(72) Inventors: Gert Sinn, Berlin (DE); Klaus-Henrik Mittenzwey, Berlin (DE)

(73) Assignee: L.U.M. GMBH, Berlin (DE)

( * ) Notice: Subject to any disclaimer, the term of this patent is extended or adjusted under 35 U.S.C. 154(b) by 186 days.

(21) Appl. No.: 14/782,755

(22) PCT Filed: Apr. 7, 2014

(86) PCT No.: PCT/EP2014/056946
§ 371 (c)(1),
(2) Date: Feb. 12, 2016

(87) PCT Pub. No.: WO2014/162014
PCT Pub. Date: Oct. 9, 2014

(65) Prior Publication Data
US 2016/0153902 A1    Jun. 2, 2016

(30) Foreign Application Priority Data
Apr. 6, 2013    (DE) .................. 10 2013 005 954

(51) Int. Cl.
*G06K 9/74*    (2006.01)
*G01N 21/47*    (2006.01)
(Continued)

(52) U.S. Cl.
CPC ......... *G01N 21/4738* (2013.01); *G01N 21/41* (2013.01); *G01N 21/53* (2013.01);
(Continued)

(58) Field of Classification Search
CPC ........... G01N 15/0205; G01N 15/0211; G01N 21/41; G01N 21/47; G01N 21/532; G01N 21/55
See application file for complete search history.

(56) References Cited

U.S. PATENT DOCUMENTS 7,271,883 B2 * 9/2007 Newell .................. G01N 21/43
356/436
8,355,121 B2    1/2013 Mittenzwey et al.
(Continued)

FOREIGN PATENT DOCUMENTS

DE    196 47 222 C1    6/1998
DE    199 20 184 A1    11/2000
(Continued)

OTHER PUBLICATIONS

International Search Report (PCT/ISA/210) dated Oct. 13, 2014, by the European Patent Office as the International Searching Authority for International Application No. PCT/EP2014/056946.
(Continued)

*Primary Examiner* — Michael A Lyons
*Assistant Examiner* — Maurice Smith
(74) *Attorney, Agent, or Firm* — Buchanan Ingersoll & Rooney PC (57) ABSTRACT

The invention relates to a device for measuring the scattering of a sample. Said device includes at least one first and one second scattering receiver for capturing scattered rays from the sample; and at least one imaging element via which rays can reach the sample and from the sample to the scattering receiver. According to the invention, the first and second scattering receivers are arranged in a common flat or approximately spherically curved surface, which is oriented perpendicular to an optical axis of the imaging element. The first scattering receiver is designed and arranged to capture saturated scattered rays from the sample and the second
(Continued)

scattering receiver is designed and arranged to capture linearly scattered rays from the sample.

36 Claims, 7 Drawing Sheets

(51) Int. Cl.
*G01N 21/53* (2006.01)
*G01N 21/41* (2006.01)
*G01N 21/55* (2014.01)
*G01N 21/59* (2006.01)

(52) U.S. Cl.
CPC .............. *G01N 21/55* (2013.01); *G01N 21/59* (2013.01); *G01N 2201/0636* (2013.01); *G01N 2201/0638* (2013.01)

(56) References Cited

U.S. PATENT DOCUMENTS

| | | | |
|---|---|---|---|
| 8,872,133 B2 | 10/2014 | Schreiber et al. | |
| 2009/0225215 A1* | 9/2009 | Korenaga | G02B 3/0068 348/340 |
| 2009/0251688 A1* | 10/2009 | Mittenzwey | G01N 21/55 356/73 |
| 2010/0282982 A1 | 11/2010 | Schreiber et al. | |
| 2012/0057172 A1 | 3/2012 | Brunfeld et al. | |
| 2012/0080611 A1* | 4/2012 | Jones | G01J 1/0242 250/458.1 |
| 2012/0305775 A1* | 12/2012 | Krolak | G02B 5/021 250/353 |
| 2015/0288861 A1* | 10/2015 | Duparr | H04N 5/3696 348/218.1 |

FOREIGN PATENT DOCUMENTS

| | | |
|---|---|---|
| DE | 100 32 739 A1 | 1/2002 |
| DE | 101 18 671 A1 | 10/2002 |
| DE | 10 2004 018 754 A1 | 11/2005 |
| DE | 10 2009 020 252 A1 | 11/2010 |
| EP | 2 249 145 A2 | 11/2010 |

OTHER PUBLICATIONS

Written Opinion (PCT/ISA/237) dated Oct. 13, 2014, by the European Patent Office as the International Searching Authority for International Application No. PCT/EP2014/056946 (with English language translation, 12 pages).

\* cited by examiner

DEVICE FOR MEASURING THE SCATTERING OF A SAMPLE

DESCRIPTION

The invention relates to an optical apparatus for measuring the scattering of a sample according to the preamble of claim 1.

Devices of this type have long been known and are used for example in the field of analytics, environmental, quality and process monitoring. Refraction serves the detection of refractive index-related substances (e.g. sugar in beverages). The absorption yields information about absorbing materials (e.g. aromatic hydrocarbons in water), the elastic scattering about scattering particles (e.g. fat in milk) and the inelastic scattering about fluorescent substances (e.g. uranin in water).

DE 199 20 184 A1 describes a device for the detection of diffuse and specular reflection of substantially opaque samples. DE 10 2004 018 754 A1, however, discloses an apparatus for measuring the scattering and absorption of substantially transparent samples. In both devices radiation divergently falls on an imaging lens and strikes the sample as a parallel bundle of rays. For transparent samples such incident radiation reaches the mirror arranged downstream of the sample and is reflected back into the sensor. By the lens the radiation transmitted through the sample is directed towards a receiver. In case of opaque samples substantially the radiation specularly reflected from the sample-side interface of the protection element falls on the receiver yielding information about the refraction. Receiver and radiation source are located in a common plane (radiation and receiving plane). Receiver and radiation source may also cover the end faces of optical fibers. Besides the radiation specularly reflected from the sample-side interface of the protection element, the receiver is applied with further radiation (i) reflected by the inner surface of the protection element, (ii) reflected by the mirror in case of transparent samples, and (iii) scattered by the sample. These are disorders that prevent a precise measurement of refraction.

In U.S. Pat. No. 8,355,121 B2, therefore, a sensor-technical device is described which allows the synchronous measurement of the refraction, scattering and absorption of samples without the mentioned disadvantage concerning the refraction measurement. The basic structure of this device is similar to the above devices. Radiation source, transmission receiver and a scattering receiver are located in the radiation- and receiving plane, which sits in the focal plane of the lens. A further scattering receiver is located within the single focal length, near the lens and beyond its optical axis. In addition, a further radiation source (refraction radiation source) is located between the radiation—and receiving plane and the lens. This radiation source is also located within the single focal length of the lens and beyond its optical axis applying the protection element and sample. The radiation specularly reflected from the sample-side interface of the protection element is detected by a further receiver, which is located on the sensor side beyond the simple focal length and the optical axis of the lens. The radiation specularly reflected from the sensor-side interface of the protection element does not fall on any receiver and does not interfere with the measurement accordingly. Disturbing scattered radiation, which falls on the refraction receiver, can be corrected with the measurement of the scattering by the scattering receiver. Compared to above-mentioned arrangements the refraction can hereby be determined without major disruption.

In DE 10 2009 020 252 B4 a very similar technical sensor device for the measurement of fluorescent radiation is used, which also describes the measurement of reference radiation. Reference radiation are photon branch currents, which are coupled out of the excitation beam being proportional to the intensity of the excitation radiation. They serve to compensate for intensity fluctuations and drifts of the source of radiation. The reference photons are directed substantially by additionally mounted beam splitter on optoelectronic receiver (reference receiver). The beam splitter is located between the radiation source and the imaging element.

Because of the possibility of determining a plurality of optical parameters by a single measurement, devices of this kind have on the one hand the great advantage of being able to solve a lot of different and complex measurement tasks. On the other hand, there is a fundamental technical difficulty. The individual components of the system have to be arranged such (i) that they do not affect themselves mutually and that any external influences (e.g. temperature) act on the components equally to perform simple compensations, and (ii) that in order to secure data interpretation simple mathematical relationships between the scattered radiation and the extinction of the sample should be valid as well as that a measured radiation is not or only slightly disturbed by another radiation. In case these points are not considered sufficiently well, this always leads to inaccuracies in the detection of refraction and/or scattering and/or absorption of a sample. This limits the versatility.

Accordingly, there is the task to realize a device for synchronous measurement of refraction and/or scattering and/or absorption of the sample, which is characterized by a higher accuracy and thus by a higher versatility.

According to the invention the following features are recognized as disadvantageous. The elements used such as radiation source, refraction radiation source, scattering receiver, refraction receiver and reference receiver and/or their associated optical fiber end faces are mostly located in different places within the sensor. Only radiation source, transmission receiver and a scattering receiver are located in a plane. Such a complex heterogeneous structure within a sensor has the effect that each component can have a life of its own (e.g. due to temperature gradients within the sensor) and thus the various radiations measured are no longer comparable, which entails greater inaccuracies in the calibration by itself. In addition, the manufacturing cost is high for such a complex and heterogeneous structures.

Further the way of detecting the reference radiation is regarded as disadvantageous. This radiation is coupled out within the optical system between the radiation source and imaging element. So this reference is primarily suitable for the detection of intensity fluctuations and drift of the radiation source. Changes in the transmission of the downstream optics (e.g. due to aging, mechanical stresses in adhesive bonds, thermal influences, etc.) cannot be detected. Moreover, there is the risk that unwanted scattered radiation from the sample falls through the channel of the incident radiation on the reference receiver.

The measurement of refraction is also in need of improvement. The refraction receiver in devices according to U.S. Pat. No. 8,355,121 B2 also receives scattering from the sample. This is a failure and it is proposed there for a correction to use the scattering determined by a separate scattering receiver. Said separate scattering receiver is not located in the immediate vicinity of refraction receiver which, however, would be advantageous for the measurement of a scattering, which should represent the scattering falling on the refraction receiver. This circumstance may in certain applications (e.g. at varying particle sizes) lead to inaccuracies in the detection of refraction.

It has been recognized further the following fact concerning scattering measurement. The scattering receiver located within the single focal length of the lens and outside its optical axis, is applied with scattered radiation from a sample volume (scattering volume) which is located behind the sensor-side protection element. This scattering volume is on the one hand determined by the superposition of the volume of the incident radiation coupled into the sample and the volume covered by the scattering receiver. On the other hand, this scattering volume is also determined by the extinction of the sample. The extinction represents the attenuation of radiation as a result of scattering and absorption in the sample and characterizes the optical density. In the case of transparent samples, the extent and/or the length of the scattering volume is (along which the incident radiation propagates) constant because the penetration depth of the incident radiation in the sample is always greater than the length of the scattering volume. In the case of samples with a low level of transparency, the incident radiation penetrates only slightly into the sample. The scattering volume becomes smaller, is dependent on the extinction of the sample and is therefore no longer constant. Both cases are characterized by different relationships between the scattered radiation and the extinction of the sample. This makes the interpretation of data or the creation of calibration for practical applications difficult. In addition, it is considered disadvantageous that the scattering receiver located within the single focal length of the imaging element covers a scattering, which is characterized by a larger range of scattering angles. Thus, the scattering cannot be matched to a particular direction. However, the measurement at different and defined scattering angles is useful, for example, in the monitoring of particle concentrations: When changing particle sizes, then the scattering intensity also changes. The scattering intensity is no longer solely dependent on the particle concentration. A particle concentration may be determined that does not correspond to the true value. Since the angle-dependent scattering is a function of particle size, it could be possible to compensate the described disorder by a measurement of the scattering at different angles.

In addition, the following appears. If scattering and transmission are to be measured simultaneously, then the scattering receiver registers backscattering from the incident radiation transmitted to the mirror as well as forward scattering from the incident radiation reflected back by the mirror. With increase of the particle concentration, initially the measured scattering intensity increases. Upon further increase. the transmitted incident radiation does not reach the mirror. Thus, the scattering receiver registers no more forward scattering. The measured scattering intensity decreases. Thus, there is no clear correlation between the scattering and the extinction of the sample.

The above objective is achieved according to the invention with an apparatus for measuring the scattering of a sample characterized in that the first and the second scattering receiver are disposed in a common plane or at least in a approximately spherically curved surface, which is oriented perpendicular to an optical axis of the imaging element, wherein the first scattering receiver is adapted and arranged to receive saturated scattered radiation of the sample and the second receiver for receiving linear scattered radiation of the sample.

The spherically curved surface is arranged symmetrically in particular with respect to the optical axis. For example, a segment of the optical axis forms a radius of curvature of the surface.

According to an embodiment of the invention, the device also includes a refraction receiver for receiving radiation specularly reflected from a sample-side interface and/or at least one transmission receiver for receiving a radiation transmitted through the sample, wherein the refraction receiver and/or the transmission receiver are arranged in the surface of the scattering receivers.

In addition, a radiation source can be disposed in the surface of the scattering receivers. For example, the surface, in which the scattering receivers are arranged, is located in the focal plane of the imaging element. In particular, the radiation source is constructed and arranged in such a manner, that a predetermined volume of the sample can be irradiated with it. It is also conceivable that the first scattering receiver is arranged so that it receives scattered radiation from a larger volume of the sample than the second scattering receiver.

Specifically, the second scattering receiver is arranged so that it receives scattered radiation from a predetermined volume of the sample. Here, the predetermined volume can be determined by the fact that the cross-section of the radiation generated by the radiation source and/or the scattered radiation is set with a diaphragm. It is also possible that the predetermined volume is determined by the distance of the imaging element to the common surface and/or to the sample.

For the generation and detection of linear and saturated scattered radiation, defined sizes of volumes of the sample are irradiated by the incident radiation as well as are detected by the scattering receiver. The linear scattered radiation is related to a sufficiently small volume and the saturated scattered radiation is related to a sufficiently large volume of the sample. As mentioned, this may be done on the one hand by inserting a diaphragm or multiple diaphragms having a defined aperture into the beam paths. This can also take place on the other hand by adjusting defined distances of the imaging element to the radiation- and receiving plane and/or to the sensor-side protection element.

Basically, it is possible with these measures to reduce parasitic radiation within the sensor, thereby optimizing the measurement of refraction, scattering and transmission radiation. In particular, the size of the scattering volume of the sample can thus be optically set. This may on the one hand have the advantage that, e.g. in samples with high extinction due to scattering, the scattering volume of the sample can be made sufficiently small to produce and measure a linear scattering at all. A further advantage is, e.g. on the other hand that the functional behavior of the intensity of the linear scattered radiation, the saturated scattered radiation and the transmitted radiation is controllable. Dynamic range, signal-to-noise ratios and working ranges can so easily be optimized.

For example, the first scattering receiver is arranged closer to the radiation source than the second scattering receiver. It is conceivable, in particular, that the second scattering receiver is positioned closer to the refraction receiver than the first scattering receiver, whereby in particular the first scattering receiver is arranged in the immediate vicinity of the radiation source and the second scattering receiver in the immediate vicinity of the refraction receiver.

In another embodiment of the invention, the device comprises at least one first protection element, which is to be located on a side of the sample faced to the scattering receivers and/or a second protection element, which is to be located on a side of the sample faced away from the scattering receivers.

The apparatus may also comprise a reflector, which is to be arranged on a side of the sample faced away from the scattering receivers. For example, the reflector is formed specularly or diffusely reflective. It is also conceivable that the transmission receiver receives radiation which is reflected back through the sample by the reflector arranged behind the second protection element.

According to another embodiment, the inventive device comprises at least one reference receiver, which is arranged in the surface of the scattering receivers. For example, the device comprises a reflector which is applied with incident radiation of a further radiation source arranged in the surface of the scattering receivers, whereby the reference receiver receives the radiation reflected by the reflector. The intensity of the incident radiation of the further radiation source may be proportional to the intensity of the incident radiation of the radiation source for application the scattering receivers.

According to another embodiment of the device, sensor-side radiation sources and receivers are arranged in a common radiation and receiving plane, and at least one imaging element and a protection element are arranged downstream in such a way that the following radiations can be received by the receivers. For a reference receiver, a radiation is essentially receivable which is reflected from sensor-side interfaces. For a refraction receiver, a radiation is essentially receivable which is reflected from sample-side interfaces. For at least one scattering receiver, a saturated scattered radiation of the sample is essentially receivable which is scattered at a defined angle to the incident radiation. For at least one further scattering receiver, a linear scattered radiation of the sample is essentially receivable which is scattered at a defined angle to the incident radiation. For a transmission receiver, a radiation is essentially receivable which is transmitted through the sample. The receivers are optionally used.

By the apparatus according to the invention it can be achieved that (i) the sensor is characterized by a slight complex structure concerning the arrangement of its elements, (ii) a reference can be detected which is representative for the entire optical system and free of interfering scattering, (iii) the refraction can be better corrected concerning the scattering, (iv) a scattering can be detected, which is free of interferences, easy evaluable and measurable under various well-defined angles, and (v) a transmission measurement can easily be added and carried out without disturbing the scattering measurement. This leads to a higher accuracy and thus to an increasing of the versatility of the sensor. When speaking of a "saturated scattered radiation", then it is meant that the scattering volume of the sample covered by the scattering receiver is not limited, and thus infinite for the scattering receiver. This scattered radiation is no longer dependent on the extent of the scattering volume but only on the extinction of the sample.

The intensity of the saturated scattered radiation is a simple function of the ratio of scattering coefficient and extinction coefficient. In case of the linear scattered radiation, the scattering volume of the sample covered by the scattering receiver is limited, and thus finite for the scattering receiver. This scattered radiation is thus dependent on the extent of the scattering volume. The intensity of the linear scattered radiation is a simple linear function of the scattering coefficient. When speaking of "directed scattered radiation", then it is meant that the scattered radiation covered by the scattering receiver is characterized by a defined angle to the incident radiation. Scattering essentially means that beside the elastic scattering the inelastic scattering can also be meant. A form of this is, e.g. the fluorescence. When speaking of "optionally using of the receiver located in the common radiation and receiving plane", then it is meant also that the inventive device can be used for the measurement of, for example, only one quantity, for example the refraction. It depends on the specific application, which quantities are actually measured. It means further that depending on the selected receiver the radiation sources are optionally used. The common surface (radiation and receiving plane) may be formed either flat or curved. A sample-side interface can be, e.g. the sample-side interface of the protection element or also downstream interfaces, e.g. surfaces of solid samples. Sensor-side interfaces are arranged between the radiation and receiving plane and the protection element and can be, e.g. the sensor-side interface of the protection element, interfaces of the imaging element or additionally introduced interfaces. When speaking of "reflected radiation", then it is meant that it can be specular or diffuse reflected radiation.

In a preferred embodiment of the invention, the imaging element is formed of two lenses of the same focal length. Here, the radiation and receiving plane is located in the focal planes of the two lenses whose optical axes are parallel to each other and aligned perpendicular to the radiation and receiving plane and to the sensor-side protection element. A radiation source is arranged outside the optical axis of the one lens which is applied with incident radiation of this radiation source. By this lens the reference receiver and the scattering receiver for the saturated scattered radiation are applied. By the other lens the refraction receiver and the scattering receiver for the linear scattered radiation are applied. Here, the scattering receiver for the saturated scattered radiation is located in the immediate vicinity of the radiation source and the scattering receiver for the linear scattered radiation is located in the immediate vicinity of the refraction receiver. With this device, it is achieved that on the one hand the divergent incident radiation is collimated by the lens. On the other hand, the apertures of the receivers are also collimated which means that the scattering receivers are essentially applied with parallel scattered radiation of the sample at defined angles to the incident radiation.

A further advantageous embodiment of the invention consists in that a further radiation source and a further receiver as a transmission receiver are arranged in the common radiation and receiving plane. The radiation source is located in the immediate vicinity of the optical axis of the one lens, which is applied with incident radiation of this radiation source. The radiation couples into the sample by this lens. A further protection element with a downstream reflector is located opposite to the sensor-side protection element. By this reflector and the same lens for the transmission receiver a radiation is essentially receivable which is transmitted through the sample. This ensures that the transmission radiation does not disturb the scattering measurement.

In a further embodiment, the radiation source is spaced from the optical axis of the one lens and the transmission receiver is spaced from the optical axis of the other lens in such a way that the transmission receiver is admittable by the other lens. That is, the coupling with respect to the transmission is carried out via the one lens and the measurement of the transmission is carried out by the other lens. Thus, coupling and measurement with respect to the transmission are locally apart from each other in the radiation and receiving plane. This has the advantage, for example, that the incident radiation specularly reflected from the one lens does not fall as a fault on the transmission receiver.

According to another embodiment of the invention, the reflector for the transmission measurement can be specularly or diffusely reflective. Here a specular reflective reflector, e.g. a mirror, usually used. A diffusely reflecting reflector is useful, if the sample is transparent and long paths of the radiation in the sample are necessary. A diffuse reflector is less susceptible with respect to possible misalignments as a mirror.

In a further embodiment of the invention a reflector is admittable with incident radiation of a further radiation source and for the reference receiver a radiation reflected from the reflector is receivable. Reflector, radiation source and reference receiver are located in the radiation and receiving plane. The intensity of the incident radiation is proportional to the intensity of the incident radiation with respect to refraction, scattering and transmission. The reference radiation for the reference receiver is generated by this reflector. Such a reflector may be specularly or diffusely reflective, and is advantageous, if the reference radiation cannot be used by other sensor-side interfaces, e.g. the sensor-side interface of the protection element.

In a preferred embodiment of the invention a partly transparent mirror is downstream of the one lens in such a way that a part of the incident radiation for refraction and scattering penetrates this mirror and couples into the sample. A part of the saturated scattered radiation of the sample is reflected by this mirror for applying the scattering receiver for the saturated scattered radiation by said lens. The radiation source and the receiver for the saturated scattered radiation are thereby locally apart from each other in the radiation and receiving plane. This has the advantage, for example, that the incident radiation specularly reflected from the one lens does not fall as a fault on the scattering receiver. Moreover, the volume of the sample irradiated by the incident radiation and the volume of the scattering of the sample detected by the scattering receiver can be optimally superimposed.

Another embodiment of the invention is that the imaging element may be formed as a single piece or multi-piece. The imaging element can be composed of a single lens or of more than two lenses. In the case of single-lens imaging element, the number of lenses used is smaller and the sensor becomes smaller. In the case of an imaging element, e.g. composed of three lenses, beside the saturated scattered radiation two linear scattered radiation at different scattering angles can be measured. Thus, the scattering properties of the sample can be better detected, enabling, for example, more accurate concentration determinations at varying particle size distributions.

The scattering receivers are arranged, e.g. along a surface having a spherical curvature facing away from the imaging element so that one of the scattering receivers arranged closer to the optical axis of the imaging element exhibits a greater distance from a center plane of the imaging element than one of the scattering receivers located further away from the optical axis of the imaging element.

In case the scattering receivers are located in a plane common surface, it is conceivable that they are arranged along a straight line that intersects an optical axis of the imaging element.

The following is a description of embodiments of the invention with reference to the figures.

Figure 1:
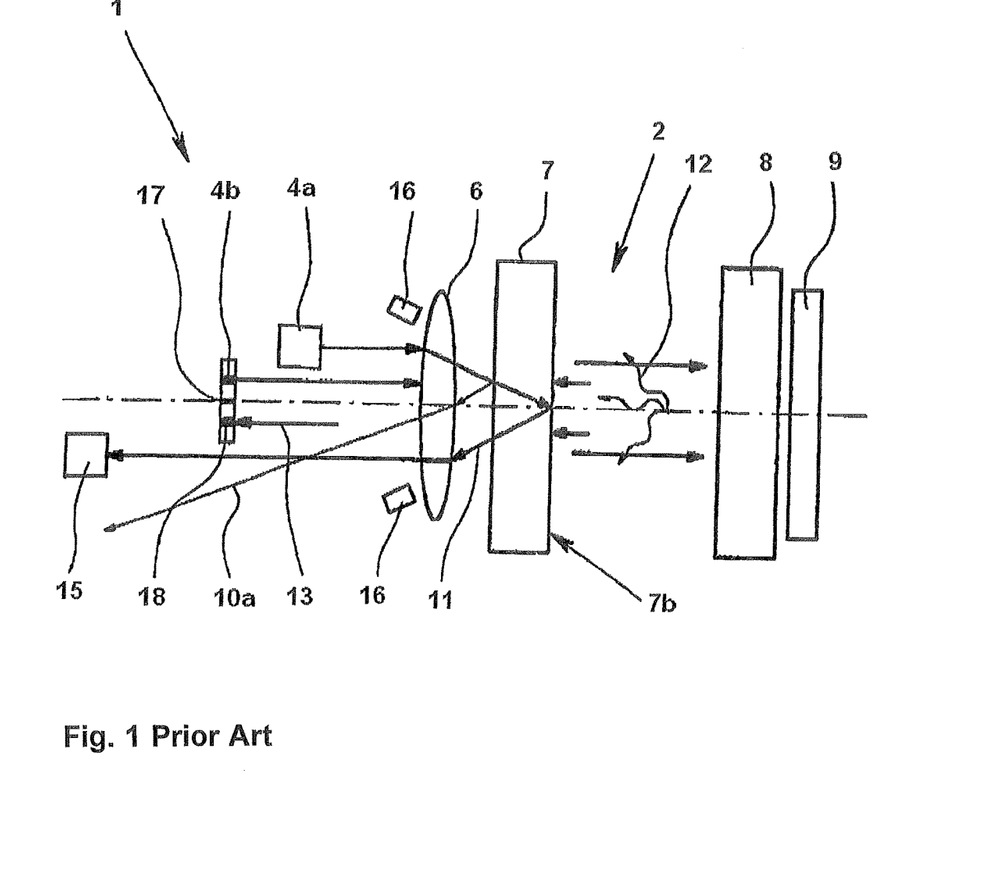
FIG. 1: Prior art device for the synchronous measurement of the refraction and/or scattering and/or absorption of a sample.

FIG. 1 shows the state of the art for measuring the scattering and/or absorption and/or refraction of a sample 2. The apparatus comprises radiation sources 4a, 4b, a refraction receiver 15, scattering receivers 16, 17 and a transmission receiver 18, and an imaging element 6, protection elements 7, 8 and mirror 9. The radiation source 4b, the scattering receiver 17 and transmission receiver 18 are arranged in the focal plane of the imaging element 6. The radiation source 4a and the scattering receiver 16 are arranged within the single focal length of the imaging element 6. The refraction receiver 15 is arranged outside the single focal length of the imaging element 6. This means that for the refraction receiver 15 the radiation 11 specularly reflected from the sample-side interface 7b of the protection element 7 is receivable. For the scattering receivers 16, 17 the scattered radiation 12 of the sample 2 is receivable. For the transmission receiver 18 the radiation 13 transmitted through the sample 2 is receivable.

According to the FIG. 2 to FIG. 6 radiation sources and receivers are arranged in a common radiation and receiving plane 3 within the sensor 1 in such a way, and at least one imaging element 6 and a protection element 7 are arranged downstream in such a way that the following radiations can be received by the receivers. For a reference receiver 14 a radiation is essentially receivable which is reflected from sensor-side interfaces. For a refraction receiver 15 a radiation is essentially receivable which is reflected from sample-side interfaces. For at least one scattering receiver 16 a saturated scattered radiation of the sample 2 is essentially receivable which is scattered at a defined angle to the incident radiation. For at least one further scattering receiver 17 a linear scattered radiation of the sample 2 is essentially receivable which is scattered at a defined angle to the incident radiation. For a transmission receiver 18 a radiation is essentially receivable which is transmitted through the sample 2. The receivers are optionally used. The sensor 1 is thus simpler, less susceptible to faults and more compact. By means of the reference receiver 14 also changes of the transmission of the optics (due to aging, mechanical stresses in adhesive bonds, thermal influences, among other things) can be detected. By means of the linear scattering the refraction receiver 15 disturbed by scattered radiation can be corrected well. The linear and saturated scattered radiation measured by this device exhibit simple relations to the extinction of the sample 2 and are therefore evaluable in a simple manner. The scattering 12 of the sample 2 is detected at two different angles to the incident radiation which provides additional information about the scattering behavior of the sample 2. Moreover the device is suitable for adding and carrying out a transmission measurement without disturbing the scattering receivers 16, 17. Radiation sources and receivers may be arranged in the radiation and receiving plane 3 directly or/and as end faces of optical fibers. In the case of end faces of optical fibers the one optical fibers carry the radiation of the radiation sources into the radiation and receiving plane 3 and the other fibers transport the radiation received in the radiation and receiving plane 3 away from it.

Figure 2:
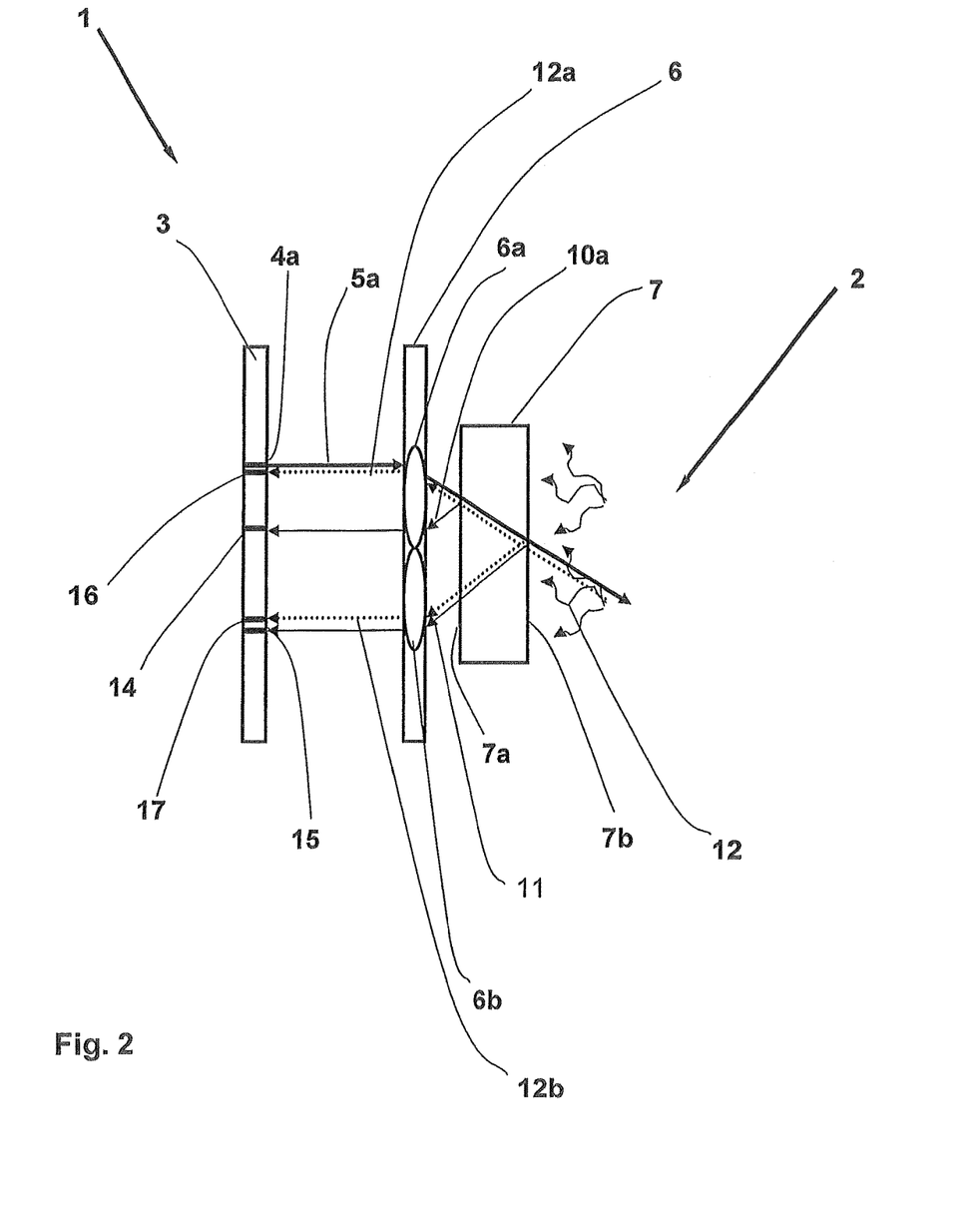
FIG. 2: Device according to a first embodiment of the invention for the synchronous measurement of the refraction and/or scattering and/or absorption of a sample with an imaging element composed of 2 lenses.

In FIG. 2, a device according to the invention is shown wherein the imaging element 6 is formed of two lenses 6a, 6b of the same focal length. Here, the radiation and receiving plane 3 is located in the focal planes of the two lenses 6a, 6b, whose optical axes are parallel to each other and aligned perpendicular to the radiation and receiving plane 3 and to the protection element 7. A radiation source 4a is arranged outside the optical axis of the lens 6a which is admittable with incident radiation 5a. By lens 6a the incident radiation 5a enters the sample 2 with a change of direction. By the lens 6a the reference receiver 14 and the scattering receiver 16 are admittable. By the lens 6b the refraction receiver 15 and the scattering receiver 17 are admittable. Here, the scattering receiver 16 is located in the immediate vicinity of the radiation source 4a and the scattering receiver 17 is located in the immediate vicinity of the refraction receiver 15. With this device, it is achieved that on the one hand the divergent incident radiation 5a is collimated by the lens 6a. On the other hand, by the lenses 6a, 6b the apertures of the receivers are also collimated, which means that the scattering receivers 16, 17 are essentially applied with parallel scattered radiations 12a, 12b of the sample 2 at defined angles. Because of the close proximity of the radiation source 4a and scattering receiver 16 it is ensured that the volume in the sample 2 irradiated by the incident radiation 5a and the volume of the sample 2 detected by the scattering receiver 16 are sufficiently well superimposed. This is needed for measuring a well formed saturated scattered radiation 12a. In contrast to this, the scattering receiver 17 detects only a small part of the volume of sample 2 irradiated by the incident radiation 5a. This kind of scattering is therefore a linear scattered radiation. This section of the linear scattered radiation 12b is located in this embodiment in the immediate vicinity of the protection element 7. Because of the close proximity of the scattering receiver 17 and refraction receiver 15 it is achieved that the refraction can be better corrected concerning the scattering. Furthermore, by means of the apparatus of the invention, with respect to reference and refraction the radiation 10a, 11 specularly reflected from the interfaces 7a and 7b are recorded separately by the receivers 14, 15 in the common radiation and receiving plane 3 in a simple manner.

Figure 3:
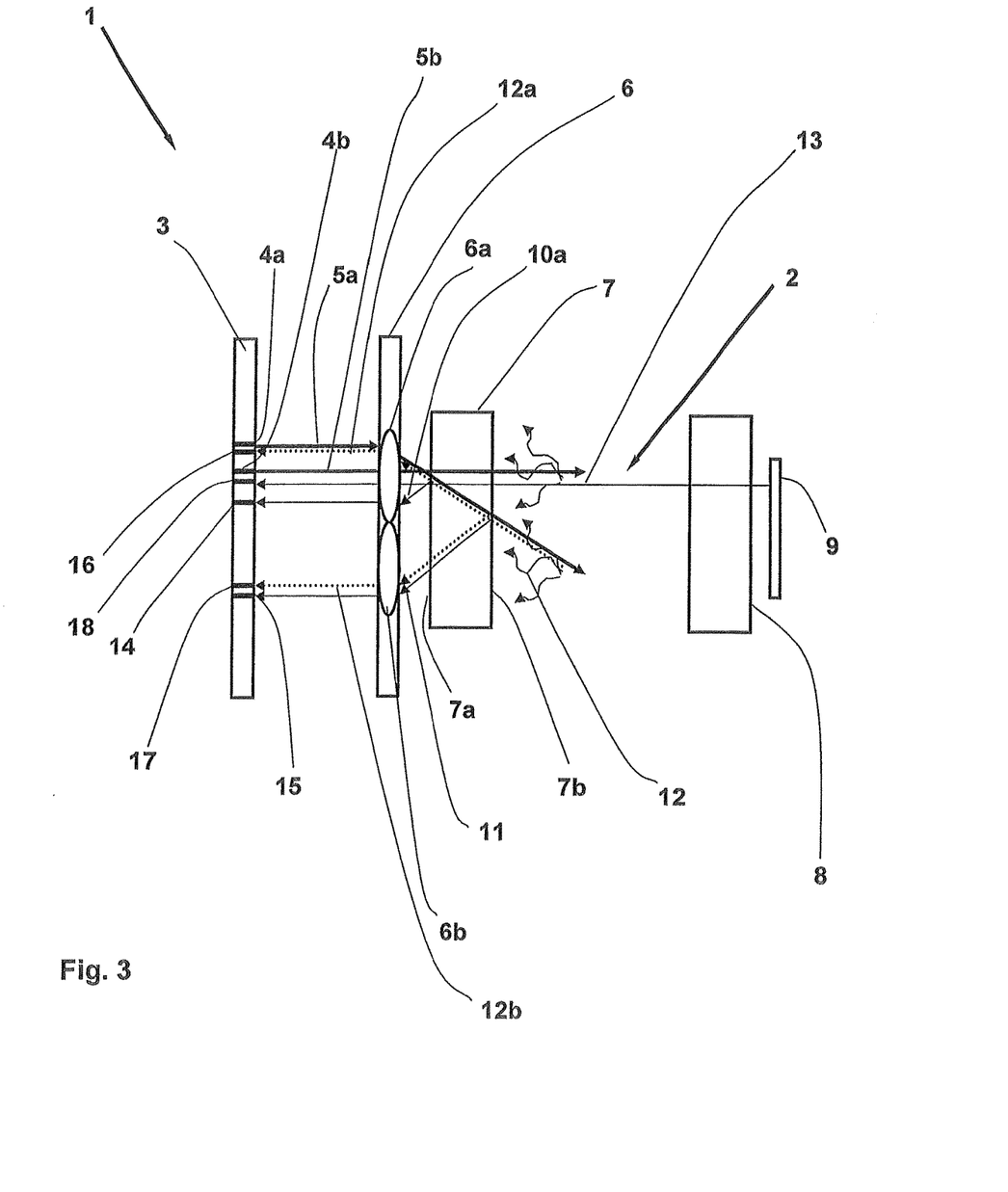
FIG. 3: Device according to a second embodiment of the invention for the synchronous measurement of the refraction and/or scattering and/or absorption of a sample with an imaging element composed of 2 lenses and transmission measurement.

FIG. 3 shows a device according to the invention, wherein a further radiation source 4b and a further receiver as a transmission receiver 18 are arranged in the common radiation and receiving plane 3 in the immediate vicinity of the optical axis of the lens 6a. The lens 6a is admittable with incident radiation 5b. By the lens 6a the collimated incident radiation 5b enters the sample 2 without a change of direction. Thereby, the incident radiation 5b can travel long distances through the sample which increases the sensitivity of the transmission measurement. A further protection element 8 with a downstream reflector 9 is located opposite to the sensor-side protection element 7. By the reflector 9 and the lens 6a for the transmission receiver 18 a radiation 13 is essentially receivable which is transmitted through the sample 2. With this arrangement, the scattering receiver 16 is not disturbed by any scattered radiation 12 generated by the transmitted radiation 13.

In a further embodiment, the radiation source 4b is spaced from the optical axis of the lens 6a and the transmission receiver 18 is spaced from the optical axis of the lens 6b in such a way that the transmission receiver 18 is admittable by the lens 6b. That is, the coupling with respect to the transmission is carried out via the lens 6a and the measurement of the transmission is carried out by the lens 6b. Thus, coupling and measurement with respect to the transmission are locally apart from each other in the radiation and receiving plane 3. This has the advantage, for example, that the incident radiation specularly reflected from the lens 6a does not fall as a fault on the transmission receiver 18.

On this basis, a further embodiment is that the reflector 9 located behind the protection element 8 can be specularly or diffusely reflective. Here a specular reflective reflector, e.g. a mirror, is usually used. A diffusely reflecting reflector is useful, if the sample 2 is transparent and long paths of the radiation in the sample are necessary. A diffuse reflector is less susceptible with respect to possible misalignments than a mirror.

Figure 4:
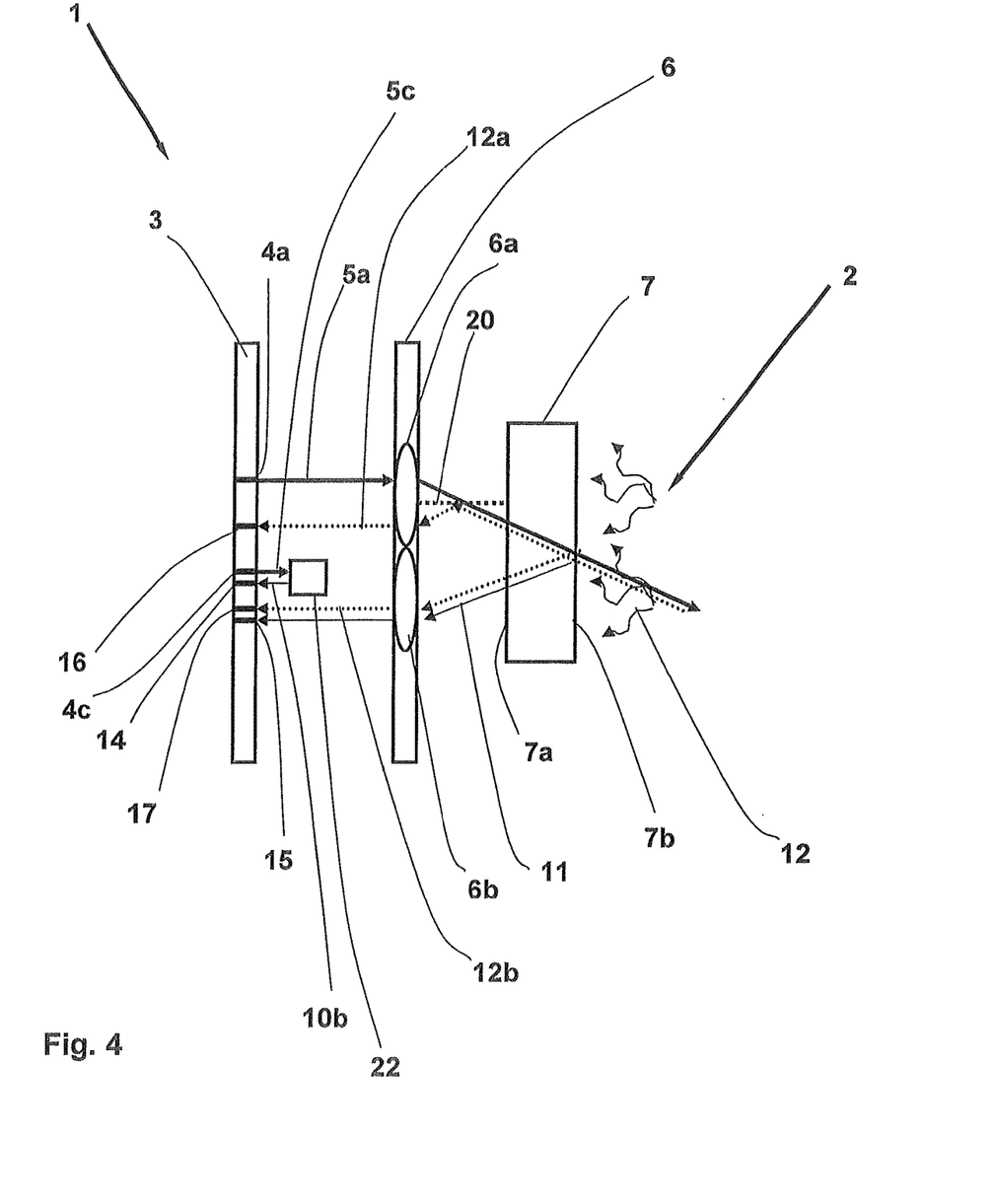
FIG. 4: Device according to a third embodiment of the invention for the synchronous measurement of the refraction and/or scattering and/or absorption of a sample with an imaging element composed of 2 lenses and modified arrangement for reference radiation and saturated scattered radiation.

FIG. 4 shows a further embodiment of the invention. A reflector 22 is admittable with incident radiation 5c of a radiation source 4c and for the reference receiver 14 a radiation 10b reflected from the reflector 22 is receivable. Reflector, radiation source and reference receiver are located in the radiation and receiving plane 3. The intensity of the incident radiation 5c is proportional to the intensity of the incident radiation 5a, 5b with respect to refraction, scattering and transmission. The reference radiation 10b for the reference receiver 14 is generated by this reflector 22. The incident radiation 5a, 5b, 5c, for example, can be originated from a common radiation source which are coupled into the one end of a fiber optic bundle. At the other end of this bundle, the optical fibers are arranged sporadically in the radiation and receiving plane 3 at the appropriate places. The reflector 22 may be specularly or diffusely reflective, and is advantageous, if the reference radiation cannot be used by other sensor-side interfaces, e.g. the sensor-side interface 7a of the protection element 7.

FIG. 4 also shows that a partly transparent mirror 20 is downstream of the lens 6a in such a way that a part of the incident radiation 5a for refraction and scattering penetrates the partly transparent mirror 20 and couples into the sample 2. A part of the saturated scattered radiation 12a of the sample 2 is reflected by the mirror 20 for applying the scattering receiver 16 by the lens 6a. The radiation source 4a and the receiver 16 for the saturated scattered radiation 12a are thereby locally apart from each other in the radiation and receiving plane 3. This has the advantage, for example, that the incident radiation specularly reflected from the lens 6a does not fall as a fault on the scattering receiver 16. Moreover, the volume of the sample 2 irradiated by the incident radiation 5a and the volume of the sample 2 detected by the scattering receiver 16 can be optimally superimposed which is particularly advantageous in case of transparent samples. In such cases, the paths necessary for the formation of a saturated scattered radiation 12a can be long. There is the risk that the volume of the sample 2 irradiated by the incident radiation 5a and the volume of the sample 2 detected by the scattering receiver 16 are no longer superimposed after a certain distance. Then scattered radiation can no longer be detected by the receiver 16.

Figure 5:
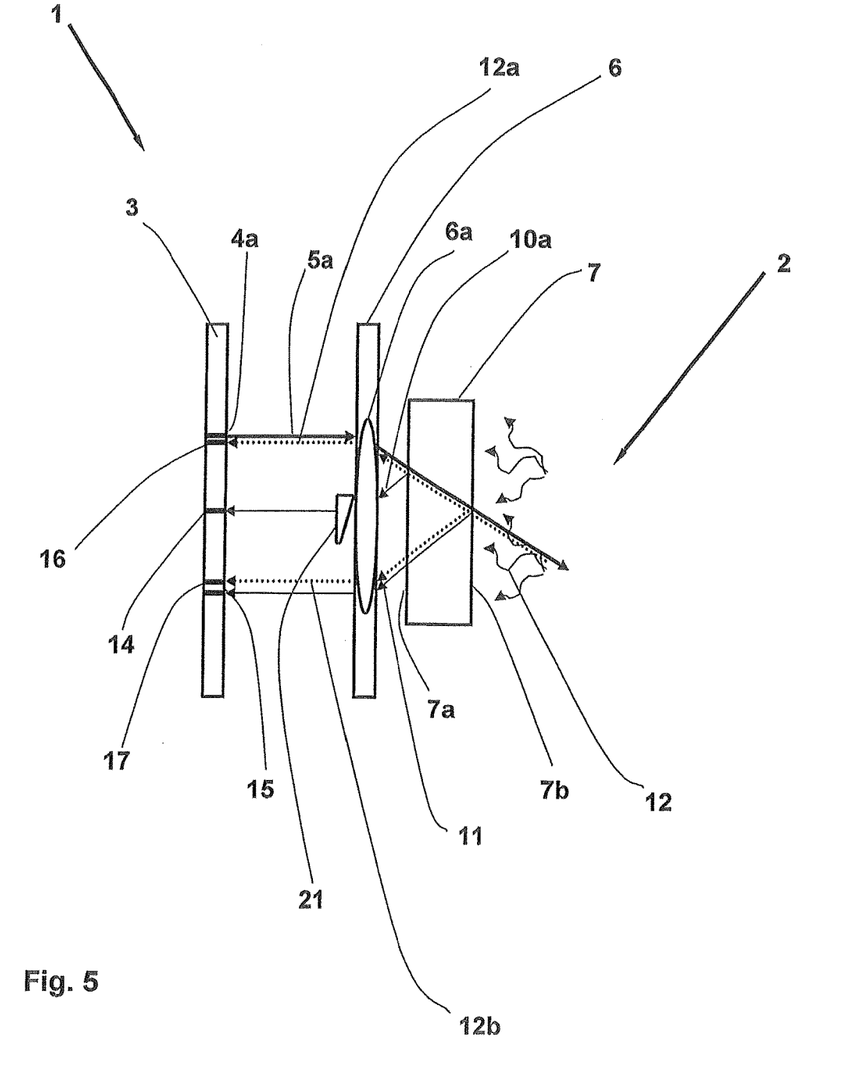
FIG. 5: Device according to a fourth embodiment of the invention for the synchronous measurement of the refraction and/or scattering and/or absorption of a sample with an imaging element composed of 1 lens.
Figure 6:
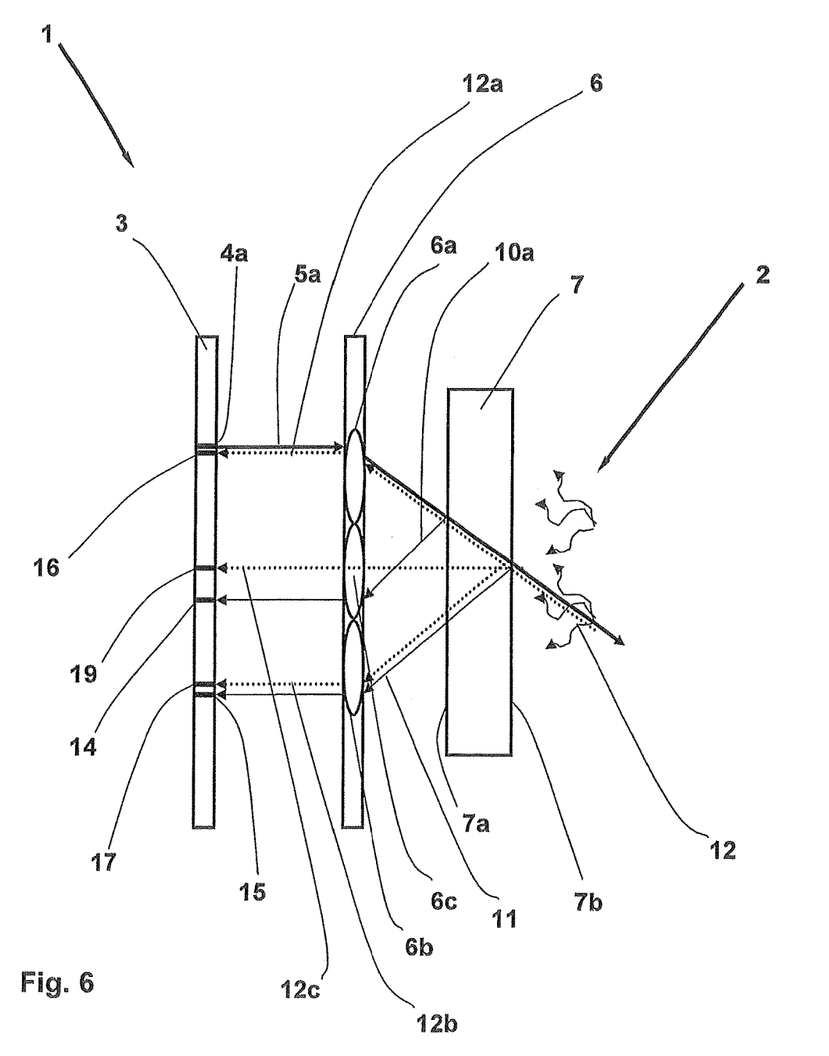
FIG. 6: Apparatus according to a fifth embodiment of the invention for the synchronous measurement of the refraction and/or scattering and/or absorption of a sample with an imaging element composed of 3 lenses.
Figure 7:
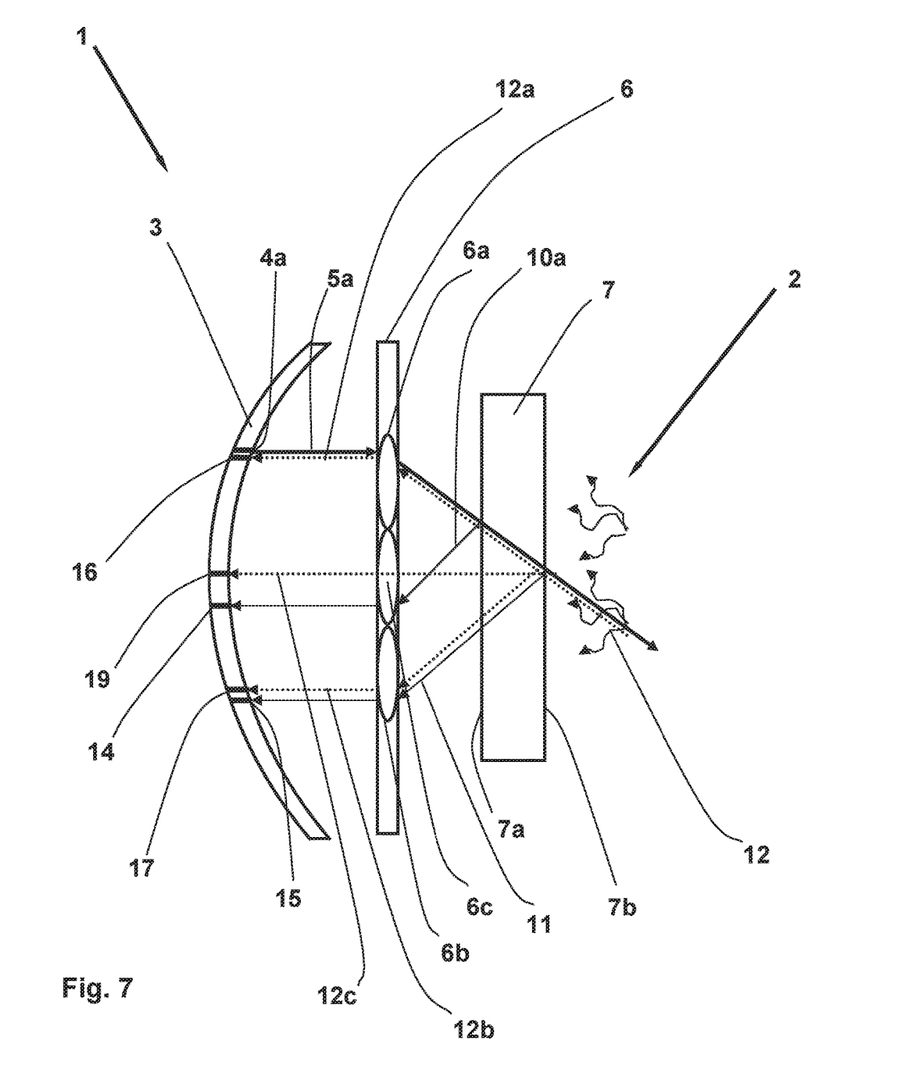

In FIGS. 5 and FIG. 6 further embodiments of the invention are shown. The imaging element 6 may be formed as a single piece or multi-piece. The imaging element 6 can be composed of a single lens 6a, or also of more than two lenses 6a, 6b, 6c. In the case of the single-lens imaging element 6 in FIG. 5, the window for beam deflection 21 serves to ensure that the reference radiation 10a is not imaged in the vicinity of the receivers 15, 17. The window 21 is for example a wedge prism. In case of the single-lens imaging element 6, the number of lenses used is smaller and the sensor becomes smaller. In the case of an imaging element 6, e.g. composed of three lenses, beside the saturated scattered radiation 12a two linear scattered radiations 12b, 12c at different scattering angles can be measured by the receivers 17, 19. Thus, the scattering properties of the sample 2 can be better detected, enabling, for example, more accurate concentration determinations at varying particle size distributions.

REFERENCE NUMERALS

1 Sensor
2 sample
3 radiation and receiving plane/surface
4a radiation source
4b radiation source
4c radiation source
5a incident radiation
5b incident radiation
5c incident radiation
6 imaging element
6a imaging element
6b imaging element
6c imaging element
7 protection element on the sensor side
7a sensor-side interface of the protection element (7)
7b sample-side interface of the protection element (7)
8 protection element on the mirror side
9 Reflector for transmission radiation
10a reflected radiation from the protection element (7), sensor side (reference radiation)
10b reflected radiation from the reflector (22) (reference radiation)
11 reflected radiation from the protection element (7), sample side (refraction radiation)
12 scattering of sample
12a scattered radiation
12b scattered radiation
12c scattered radiation
13 transmitted radiation through the sample (transmission radiation)
14 reference receiver
15 refraction receiver
16 scattering receiver
17 scattering receiver
18 transmission receiver
19 scattering receiver
20 mirror, partly transparent
21 window for beam deflection (prism)
22 reflector for reference radiation

The invention claimed is:

1. A device for measuring scattering of a sample, comprising:
at least a first scattering receiver and a second scattering receiver for receiving scattered radiation from a sample;
at least one imaging element through which radiation can pass to the sample and from the sample to the scattering receivers, and
at least one refraction receiver for receiving specularly reflected radiation from an interface of a sample; and/or at least a transmission receiver for receiving a radiation transmitted through the sample,
wherein the first and the second scattering receivers are arranged in a common plane or at least in an approximately spherically curved surface, which is oriented perpendicular to an optical axis of the imaging element, wherein the first scattering receiver is constructed and arranged for receiving saturated scattered radiation of the sample and the second scattering receiver is constructed and arranged for receiving a linear scattered radiation of the sample,
wherein the refraction receiver and/or the transmission receiver are arranged in the common plane or in the at least approximately spherically curved surface.

2. Device according to claim 1, comprising:
a radiation source which is arranged in the common plane or in the at least approximately spherically curved surface.

3. Device according to claim 2, comprising:
for measuring transmission, a further radiation source is arranged in the common plane or in the at least approximately spherically curved surface.

4. Device according to claim 3, wherein the first lens is admittable with incident radiation of the further radiation source and wherein, via the first lens, radiation reaches the transmission receiver.

5. Device according to claim 4, wherein the further radiation source and the transmission receiver are spaced from the optical axis of the imaging element in such a way that the transmission receiver is admittable with radiation from the second lens.

6. Device according to claim 5 wherein the transmission receiver is admittable with radiation from the first lens.

7. Device according to claim 1, wherein the common plane or surface where the scattering receivers are arranged, is located in a focal plane of the imaging element.

8. Device according to claim 1, wherein the first scattering receiver is arranged such that it will receive scattered radiation from a larger volume of the sample than the second scattering receiver.

9. Device according to claim 1, wherein the second scattering receiver is arranged such that it will receive scattered radiation from a predetermined volume the sample.

10. Device according to claim 9, wherein the predetermined volume from which scattered radiation is received, is a function of a cross section of the radiation generated by a radiation source or of the scattered radiation being determined with a diaphragm.

11. Device according to claim 9, wherein the predetermined volume is determined by a distance of the imaging element to the common plane or the at least approximately spherically curved surface and/or to a sample location.

12. Device according to claim 1, wherein the first scattering receiver is arranged closer to the radiation source than the second scattering receiver.

13. Device according to claim 1, wherein the second scattering receiver is arranged closer to the refraction receiver than the first scattering receiver.

14. Device according to claim 1, wherein the first scattering receiver is arranged in an immediate vicinity of the radiation source and the second scattering receiver is arranged in an immediate vicinity of the refraction receiver.

15. Device according to claim 1, comprising:
at least one first protection element, which is to be arranged on a side of the sample facing to the scattering receivers, and/or a second protection element, which is to be arranged on a side of the sample facing away from the scattering receivers.

16. Device according to claim 15, wherein for the transmission receiver a radiation is receivable, which will be transmitted back through the sample by a reflector arranged downstream of the second protection element.

17. Device according to claim 1, comprising:
a reflector, which is to be arranged on a side of the sample facing away from the scattering receivers.

18. Device according to claim 17, wherein the reflector is specularly or diffusely reflective.

19. Device according to claim 1, comprising:
at least one reference receiver which is arranged in the common plane or in the at least approximately spherically curved surface.

20. Device according to claim 19 wherein the reference receiver is arranged so that it receives radiation which is reflected at the first protection element.

21. Device according to claim 19, comprising:
a reflector, which is admittable with incident radiation of a further radiation source arranged in the common plane or in the at least approximately spherically curved surface wherein the reference receiver receives the radiation reflected by the reflector.

22. Device according to claim 21, wherein an available intensity of incident radiation of the further radiation source is proportional to an intensity of the incident radiation of the radiation source for application the scattering receivers.

23. Device according to claim 1, wherein a radiation source and the receivers are arranged in the common surface, and the imaging element and a first protection element are arranged downstream in such a way that for a reference receiver a radiation is receivable, which is reflected from a sensor-side interface of the first protection element, for the refraction receiver a radiation is receivable, which is reflected from a sample-side interface of the first protection element, for one of the scattering receivers a saturated scattered radiation of the sample is receivable, which is scattered at a defined angle to an incident radiation of the radiation source, for one of the scattering receivers a linear scattered radiation of the sample is receivable, which is scattered at a defined angle to the incident radiation, and for the transmission receiver a radiation is receivable which is transmitted through the sample and the second protection element and then reflected by the reflector and transmitted back through the sample again.

24. Device according to claim 1, wherein the imaging element is formed in one piece.

25. Device according to claim 1, wherein the imaging element is formed as a multi-piece.

26. Device according to claim 1, wherein the imaging element exhibits at least a first and a second lens, whose optical axes run parallel to one another.

27. Device according to claim 26, wherein the lenses have a same focal length.

28. Device according to claim 26, wherein the radiation source is arranged outside an optical axis of the first lens.

29. Device according to claim 28, the first lens is admittable with incident radiation of the radiation source and a reference receiver and the first scattering receiver are admittable with radiation from the first lens, and the refraction receiver and the second scattering receiver are admittable with radiation from a second lens.

30. Device according to claim 26, wherein the transmission receiver is arranged in an immediate vicinity of or on the optical axis of the first lens.

31. Device according to claim 1, comprising:
a partly transparent mirror downstream of the imaging element in such a way that a part of the incident radiation of the radiation source will penetrate this mirror, wherein a part of the saturated scattered radiation of the sample will be reflected by the mirror.

32. Device according to claim 31, arranged such that the scattered radiation is will be reflected by the mirror in such a way that the scattering receiver will be admittable with the scattered radiation by the imaging element.

33. Device according to claim 32, arranged such that the scattered radiation will be reflected by the mirror in such a way that the scattering receiver will be admittable with the scattered radiation by the first lens.

34. Device according to claim 1, wherein the radiation source is formed and arranged in such a manner that a predetermined volume of a sample will be irradiated with it.

35. Device according to claim 1, wherein the scattering receivers are arranged in the approximately spherically curved surface, wherein the approximately spherically curved surface has a spherical curvature facing away from the imaging element so that one of the scattering receivers arranged closer to the optical axis of the imaging element exhibits a greater distance from a center plane of the imaging element than one of the scattering receivers located further away from the optical axis of the imaging element.

36. Device according to claim 1, wherein the scattering receivers are arranged along a straight line which intersects an optical axis of the imaging element.

* * * * *